United States Patent
Hadfield et al.

(10) Patent No.: US 7,154,001 B2
(45) Date of Patent: *Dec. 26, 2006

(54) FORMATE SALT OF O-DESMETHYL-VENLAFAXINE

(75) Inventors: Anthony Francis Hadfield, Nanuet, NY (US); Michael William Winkley, Campbell Hall, NY (US)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/256,241

(22) Filed: Oct. 21, 2005

(65) Prior Publication Data

US 2006/0058552 A1    Mar. 16, 2006

Related U.S. Application Data

(63) Continuation of application No. 10/457,596, filed on Jun. 9, 2003, now Pat. No. 7,001,920.

(60) Provisional application No. 60/387,321, filed on Jun. 10, 2002.

(51) Int. Cl.
*C07C 53/06* (2006.01)

(52) U.S. Cl. .................................................. 562/609

(58) Field of Classification Search ................ None
See application file for complete search history.

(56) References Cited

U.S. PATENT DOCUMENTS

| | | |
|---|---|---|
| 4,535,186 A | 8/1985 | Husbands et al. |
| 6,197,828 B1 | 3/2001 | Jerussi et al. |
| 6,348,494 B1 | 2/2002 | Yardley et al. |
| 6,562,629 B1 | 5/2003 | Lin et al. |
| 2002/0054912 A1 | 5/2002 | Kim et al. |
| 2002/0086904 A1 | 7/2002 | Jerussi et al. |
| 2003/0045583 A1 | 3/2003 | Hadfield et al. |
| 2003/0206869 A1 | 11/2003 | Rabinowitz |

FOREIGN PATENT DOCUMENTS

| | | |
|---|---|---|
| EP | 0 112 669 | 7/1984 |
| WO | WO 00/32555 | 6/2000 |
| WO | WO 00/59851 | 10/2000 |
| WO | WO 00/76955 | 12/2000 |

OTHER PUBLICATIONS

Samir Cherkaoui et al., Electrophoresis, 2001, 491-496, 22.

*Primary Examiner*—Paul A. Zucker
(74) *Attorney, Agent, or Firm*—Rebecca R. Barrett (57) ABSTRACT

A novel salt of O-desmethylvenlafaxine, O-desmethylvenlafaxine formate, is provided. Pharmaceutical compositions, dosage forms and methods of use are also provided.

7 Claims, 3 Drawing Sheets

FORMATE SALT OF O-DESMETHYL-VENLAFAXINE

This application is a continuation of U.S. application Ser. No. 10/457,596, filed on Jun. 9, 2003, now U.S. Pat. No. 7,001,920, which claims benefit to Provisional Application No. 60/387,321, filed on Jun. 10, 2002, the entire disclosure of which is hereby incorporated by reference.

O-desmethyl venlafaxine is a major metabolite of venlafaxine and has been shown to inhibit norepinephrine and serotonin uptake. O-desmethylvenlafaxine, chemically named 1-[2-(dimethylamino)-1-(4-phenol)ethyl]cyclohexanol, was exemplified as a fumarate salt in U.S. Pat. No. 4,535,186. However, the fumarate salt of O-desmethylvenlafaxine has unsuitable physiochemical and permeability characteristics. O-desmethylvenlafaxine is also exemplified as a free base in WO 00/32555 and taught to be useful for the treatment of depression and a variety of other disorders.

Salt formation provides a means of altering the physiochemical and resultant biological characteristics of a drug without modifying its chemical structure. A salt form can have a dramatic influence on the properties of the drug. The selection of a suitable salt is partially dictated by yield, dissolution rate and quantity of the crystalline structure. In addition, hygroscopicity, stability, solubility and the process profile of the salt form are important considerations.

SUMMARY OF THE INVENTION

The present invention relates to a novel salt of O-desmethylvenlafaxine, O-desmethylvenlafaxine formate (hereinafter "ODV formate"). The novel salt of the present invention has properties which are particularly suitable for use as a drug. Pharmaceutical compositions comprising ODV formate and pharmaceutically acceptable carriers or excipients are also provided. Preferably, the pharmaceutical compositions comprise an amount of ODV formate effective to treat the desired indication in an animal such as a human.

In further embodiments of the invention are provided methods of treating patients suffering from depression (including but not limited to major depressive disorder, bipolar disorder and dysthymia), anxiety, panic disorder, generalized anxiety disorder, post traumatic stress disorder, premenstrual dysphoric disorder (also known as premenstrual syndrome), fibromyalgia, agoraphobia, attention deficit disorder (with and without hyperactivity), obsessive compulsive disorder (including trichotillomania), social anxiety disorder, autism, schizophrenia, obesity, anorexia nervosa, bulimia nervosa, Gilles de la Tourette Syndrome, vasomotor flushing, cocaine and alcohol addiction, sexual dysfunction, (including, but not limited to premature ejaculation), borderline personality disorder, chronic fatigue syndrome, incontinence (including fecal incontinence, overflow incontinence, passive incontinence, reflex incontinence, stress urinary incontinence, urge incontinence, urinary exertional incontinence and urinary incontinence), pain (including but not limited to migraine, chronic back pain, phantom limb pain, central pain, neuropathic pain such as diabetic neuropathy, and postherpetic neuropathy; gastrointestinal pain disorders including, but not limited to irritable bowel syndrome, symptomatic GERD, hypersensitive esophagus, non-ulcer dyspepsia, noncardiac chest pain, biliary dyskinesia, sphincter of oddi dysfunction, and genitourinary pain disorders including but not limited to interstitial cystitis (irritable bladder), and chronic pelvic pain (including, but not limited to vulvodynia, prostatodynia and proctalgia)), Raynaud's syndrome, Parkinson's Disease, epilepsy, and others comprising providing to a patient an effective amount of ODV formate. ODV formate can also be administered to prevent relapse and recurrence of depression, to induce cognitive enhancement, to treat cognitive impairment in patients suffering from senile dementia, Alzheimer's disease, memory loss, amnesia and amnesia syndrome, and in regimens for cessation of smoking or other tobacco uses.

DETAILED DESCRIPTION OF THE INVENTION

Definitions

Unless defined otherwise in the specification, the following terms have these meanings:

The term "about" generally means within 10%, preferably within 5% and more preferably within 1% of a given value or range. Alternatively, the term "about" means within an acceptable standard error of the mean, when considered by one skilled in the art.

The term "treat" as used herein refers to preventing, ameliorating, controlling or curing one or more symptoms of a disorder.

The present invention relates to the novel salt of O-desmethylvenlafaxine, O-desmethylvenlafaxine formate (ODV formate). O-desmethylvenlafaxine formate provides useful properties for formulation, and has the structural formula:

Formate salts of O-desmethylvenlafaxine (ODV) exist as enantiomers and this invention includes racemic mixtures as well as stereoisomerically pure forms of the same.

Stereoisomerically pure refers to compounds which are comprised of a greater proportion of the desired isomer than of the optical anipode. A stereoisomerically pure compound is generally made up of at least about 90% of the desired isomer based upon 100% total weight of ODV formate.

ODV free base may be prepared according to the general procedures outlined in U.S. Pat. No. 4,535,186 or as described in U.S. Ser. No. 10/073,743, the disclosures of which are incorporated by reference herein in their entirety.

As described in Reviews in Contemporary Pharmacology, Volume 9(5) page 293–302 (1998), incorporated by reference in its entirety, O-desmethylvenlafaxine has the following pharmacological profile.

|  | O-desmethylvenlafaxine |
|---|---|
| Effect (in vivo) | |
| Reversal of Reserpine-Induce Hypothermia (minimum effect; mg/kg i.p.) | 3 |
| Effect (in vitro) | |
| Inhibition of amine reuptake (IC50; uM) | |
| Norepinephrine | 1.16 |
| Serotonin | 0.18 |
| Dopamine | 13.4 |
| Affinity for Various Neuroreceptors (% inhibition at 1 uM) | |
| D2 | 6 |
| Cholinergic | 7 |
| Adrenergic a | 0 |
| Histamine H1 | 0 |
| Opiate | 7 |

ODV formate is crystalline as evidenced by NMR and XRPD analyses. The molar ratio of formate to ODV is 1:1. The proposed structure is consistent with the proton NMR spectra.

Formate salts of ODV may be formed by contacting stoiciometric amounts of an acid with O-desmethylvenlafaxine free base. Alternatively, such acid may be used in excess, usually no more than about 1.1 equivalents to 2.5 equivalents. In some methods of the invention, the base and the acid are both in solution. In other embodiments of the invention, the base is in suspension in a solvent and dissolves as formic acid is added.

In some preferred methods of the invention the free base is in a solvent such as an alcohol, acetone or tetrahydrofuran. Preferably the solvent has limited reactivity to formic acid. In some preferred embodiments of the invention, the solvent is tetrahydrofuran or 2-propanol.

A mixture of formic acid and free base is soluble in a suitable solvent or solvents at temperatures ranging from about 55° C. to about 80° C. Thereafter, crystallization may be achieved as the solution is cooled. Crystallization may be facilitated by seeding with O-desmethylvenlafaxine formate crystals. Crystallization may be optimized, for instance to achieve larger crystals, by cooling at a rate of about 1 degree per about 3–5 minutes to 5 to 6 degrees below the cloud point of about 40° C. Thus, crystallization occurs at about 34° to about 35° C. in 2-propanol. Thereafter, incubation for more than about 1 to 1 and ½ hours allows complete or nearly complete crystallization ODV formate particle size (evaluated by microscope) ranged from about 0.4 to about 165 μm and more particularly from about 1.5 to about 26 μm. Average particle size was from about 11 to about 16 μm. Particle size distribution (as measured by Malvern apparatus, 100 mm lens, Lecithin/MS dispersant) was 10% less than about 4 μm and 90% less than about 34 μm.

The aspect ratio ranged from about 1 to about 44, more particularly from about 1 to about 21 and more particularly from about 1 to about 4. Average aspect ratio was about 2. 90% of particles have an aspect ratio of less than 4.

O-desmethyl venlafaxine formate was evaluated for oral absorption characteristics. The rat intestinal perfusion model was used.

Rat Intestinal Perfusion Test

The rat intestine perfusion technique is a direct way to measure the regional absorption properties of a test compound in the gastrointestinal tract. Rat intestinal permeability coefficient (Peff) can be used to predict human in vivo oral absorption of passively absorbed compounds. Fagerholm, M. Johansson, and H. Lennernäs, "Comparison between permeability coefficients in rat and human jejunum", *Pharm. Res.*, 13, 1996, 1336–1342, have demonstrated a good correlation between rat Peff and human fraction of dose absorbed (Fa) for a series of compounds. Other characteristics such as formulable Maximum Absorbable Dose (MAD), FDA Biopharmaceutical Classification, etc. can also be estimated.

Materials

Perfusion buffer (PB) consisted of KCl (5.4 mM), NaCl (48 mM), $Na_2HPO_4$ (28 mM), $NaH_2PO_4$ (43 mM), mannitol (35 mM), polyethylene glycol (PEG)-4000 (0.1%, w/v), glucose (10 mM). The pH was adjusted to 6.8 with NaOH and osmolarity was adjusted to 290+10 mOsm/l with 1.0 M NaCl. Before the experiment, $^{14}$C-PEC-4000 (0.02 μCi/mL), 3H-mannitol (0.025 μCi/mL), metoprolol (20 μg/mL), and ODV formate or fumarate (50 μg/mL) were added.

Rats used in this study were Charles River CD males, ranging in weight from approximately 300–350 grams.

Internal Standard Compounds

Metoprolol (a well-absorbed and passively transported compound) was used as a standard and tested simultaneously along with the ODV compounds. Glucose (a well-absorbed and actively transported compound) was used to monitor the physiological functionality of the intestinal barriers. $^{14}$C-labeled PEG-4000 was used as a non-absorbable marker to describe the water flux across the intestinal wall. $^3$H-labeled mannitol was used as a paracellularly transported marker to indicate the integrity of the intestinal tight junctions.

Analytical Methods

All chemicals were of analytical grade. After each experiment, all the analytical assays were performed promptly. For isotope determinations, 0.5 mL of perfusate sample containing $^{14}$C PEG-4000 and $^3$H-mannitol was mixed with 5 mL of scintillation cocktail. Radioactivity was counted in a liquid scintillation counter (Wallac 1409). Glucose concentration was determined by the glucose oxidase method (Biochemistry Analyzer). Metoprolol and the ODV compounds were analyzed by HPLC-UV/Vis (HP-1100 with a diode-array detector), using a YMC AQ 120μ, 5μ, 150×4.6 mm column and step gradient mobile phase containing water/0.1% TFA and acetonitrile. The ODV compounds and metoprolol were detected at 226 and 272 nm UV wavelength, respectively. Blank perfusate was assayed to evaluate the interference at these chromatographic conditions.

In Situ Rat Jejunal Perfusion

The perfusions were performed in three intestinal sections of anesthetized rats: duodenum-jejunum, ileum, and colon. The lengths of the segments were approximately 10–12 cm for small intestine segments and 5–6 cm for colon segments. An inflow cannula was inserted at the proximal end and an outflow cannula was inserted at the distal end. Perfusate was pumped through the segment at 0.19 mL/min, and collected at 20, 40, 55, 70, 85 and 100 minutes.

ODV formate or fumarate was added to the perfusion working buffer at a concentration of 50 μg/mL, which is approximately equivalent to a 200 mg human dose. The disappearance rates of ODV compound, metoprolol, and glucose were determined from each collection interval by comparing to the initial compound solution remaining in the syringe at the end of the 100 minutes. This is to correct for any losses due to binding to the syringe or tubing. Meanwhile, drug concentration in perfusate samples were corrected for water influx/efflux, which was computed, based on $^{14}C$-PEG-4000 concentration changes.

Data Analysis a. Recovery and Water Flux

Recovery of $^{14}C$-PEG-4000 was determined to provide information on the integrity of the perfused intestinal segment:

$$\%PEG_{rec}=(\Sigma PEG_{out}/\Sigma PEG_{in})*100$$

Overall $^{14}C$-PEG-4000 recovery was calculated and any data for which the individual recovery fell outside of the range of 96%–103% was excluded from the data set. Values below this range would indicate tissue damage that allows passage of PEG-4000 outside of the perfused segment, while values above this range would indicate significant water movement out of the segment. Water movement across the gut wall was determined by calculation of net water flux:

$$\text{Net Water Flux } (NWF)=[(1-PEG_{out}/PEG_{in})*Q]/L$$

where $PEG_{out}$ and $PEG_{in}$ are the amount of radioactivity (dpm) of $^{14}C$-PEG-4000 in inlet and outlet sides of the perfused intestinal segment, respectively; Q is the flow rate of perfusate; and L is the length of perfused segment (cm).

b. Peff Calculation

The presence of the ODV compound in the perfusate was determined by HPLC. The amount of drug present at each time point was corrected for water movement across the wall of the intestine:

$$C_{out,corr}=C_{out}*(PEG_{in}/PEG_{out})$$

where $C_{out}$ is the concentration of drug in outlet perfusate; $C_{out,corr}$ is the concentration of drug in outlet perfusate corrected for water moving in or out of the segment, as determined by the recovery of $^{14}C$-PEG-4000.

Effective intestinal permeability, Peff (cm/sec), was determined by the following equation:

$$Peff=[Q*(C_{in}-C_{out,corr})/C_{in}]/2\mu rL$$

where Q is the flow rate; $C_{in}$ is the concentration of drug in inlet perfusate; $2\mu rL$ is the inner surface area of the perfused segment, with r assumed to be 0.18 cm in the rat (see G. Amidon, H. Lennernäs, V. Shah, J. Crison. "A theoretical basis for a biopharmaceutic drug classification: The correlation of in vitro drug product dissolution and in vivo bioavailability." *Pharm. Res.* 12, 1995, 413–420) and L the length of the perfused segment (cm).

c. Fraction Absorbed (Fa)

The fraction of dose absorbed, Fa, in human is currently predicted from (Fagerholm, M. ibid:

$$Fa=100*(1-e^{-(2*(*Peff,rat+\beta)*(tres/r)})$$

where * and * are the correction factors, tres is the residence time in human small intestine; and r is the radius of the human small intestine.

Results

Rat Jejunal Perfusion Results

Site-Specific Absorption of ODV Formate

The Peff values for ODV formate in the small intestine ($1.34\times10^{-5}$ cm/sec in duodenum-jejunum, $2.18\pm0.33*10^{-5}$ cm/sec in ileum) were lower than metoprolol=s Peff values. The Peff value of ODV formate in the colon was found to be $0.0727\times10^{-5}$ cm/sec, which is about 12% of metoprolol=s Peff value in the colon. The ileum segment seems to be the best absorption site for ODV formate. The Peff=s ratio of duodenum-jejunum vs. ileum vs. colon was found to be 1.34:2.18:0.07, indicating that small intestinal sites of duodenum, jejunum, and ileum predominate the oral absorption of this compound for an immediate release dosage form. (Dongzhou Liu, S. Ng, R. Saunders, "Effect of Polysorbate 80 on Transport of Mannitol, Glucose, and Water Flux in Rat Small Intestine", *PharmSci.*, 2, 2000; Doungzhou Liu, S. Ng, R. Saunders. "Investigating Intestinal Uptake of Zaleplon in site and Simulating/Predicting Oral Absorption in vivo", Submitted to *PharmSci.* 3(4), 2001).

Based on this experimental Peff, the human in vivo Fa of ODV formate was estimated to be about 80% in the small intestine (jejunum and ileum). The delivery vehicle was perfusion buffer (pH=6.8). The test at each absorption site was repeated with 3 rats and the Peff values were averaged.

Rat Perfusion Data of ODV Formate (50 g/ml)

| Absorption Site | $Peff_{ODV\ Formate}$ ($10^{-5}$ cm/sec) | $Peff_{Metoprolol}$ ($10^{-5}$ cm/sec) | $Peff_{ODV\ Formate}/Peff_{Metoprolol}$ |
| --- | --- | --- | --- |
| Jejunum | 1.34 | 2.50 ± 0.11 | 0.54 |
| Ileum | 2.18 ± 0.33 | 3.22 ± 0.07 | 0.68 ± 0.08 |
| Colon | 0.07 | 0.583 ± 0.087 | 0.13 |

Site-Specific Absorption of ODV Fumarate

The site-specific absorption of ODV fumarate was investigated under the same study conditions as ODV formate (50 µg/ml in pH 6.8 perfusion buffer). The test at each absorption site was repeated with 3 rats (except for in the Jejunum, where only 2 rats were tested) and the Peff values were averaged.

Rat Perfusion Data of ODV Fumarate (50 g/ml)

| Absorption Site | $Peff_{ODV\ Fumarate}$ ($10^{-5}$ cm/sec) | $Peff_{Metoprolol}$ ($10^{-5}$ cm/sec) | $Peff_{ODV\ Fumarate}/Peff_{Metoprolol}$ |
| --- | --- | --- | --- |
| Jejunum | 0.245 | 1.78 ± 0.93 | 0.09 |
| Ileum | 0.678 ± 0.295 | 5.3 | 0.19 ± 0.06 |
| Colon | 0 | 11 | 0 |

In general, the results show that ODV fumarate was less absorbed than ODV formate in the rat GI tract. In the small intestine, the Peff values of the fumarate salt (0.24 –0.68× $10^{-5}$ cm/sec) compared to ($1.34-2.18\times10^{-5}$ cm/sec) of the formate Peff values. In the colon, no measurable absorption of ODV fumarate was found. The in vivo Fa of ODV fumarate was estimated to be in the range of 33–45% in the small intestine and 0 in the colon, indicating an overall low absorption of this compound in the entire GI tract.

The results of the site-specific intestinal absorption of ODV formate and ODV fumarate show that ODV formate has better absorption in the small intestine and in the colon than ODV fumarate. Several publications have demonstrated that there is high correlation between the rat perfusion model and in vivo human absorption (see e.g., Doungzhou Liu, S. Ng, R. Saunders. "Investigating Intestinal Uptake of Zaleplon in site and Simulating/Predicting Oral Absorption in vivo", Submitted to *PharmSci.* 3(4), 2001).

The solubility of ODV formate in water is greater than 425 mg/ml at room temperature (about 25 to 27° C.). High solubility and high oral absorption are desireable characteristics of a drug, making this salt form of O desmethyl venlafaxine a particularly useful form of O-desmethyl venlafaxine.

Thus, compounds, compositions and methods of the present invention can be used to treat or prevent central nervous system disorders including, but not limited to depression (including but not limited to major depressive disorder, bipolar disorder and dysthymia), fibromyalgia, anxiety, panic disorder, agorophobia, post traumatic stress disorder, premenstrual dysphoric disorder (also known as premenstrual syndrome), attention deficit disorder (with and without hyperactivity), obsessive compulsive disorder (including trichotillomania), social anxiety disorder, generalized anxiety disorder, autism, schizophrenia, obesity, anorexia nervosa, bulimia nervosa, Gilles de la Tourette Syndrome, vasomotor flushing, cocaine and alcohol addiction, sexual dysfunction, (including premature ejaculation), borderline personality disorder, chronic fatigue syndrome, incontinence (including fecal incontinence, overflow incontinence, passive incontinence, reflex incontinence, stress urinary incontinence, urge incontinence, urinary exertional incontinence and urinary incontience), pain (including but not limited to migraine, chronic back pain, phantom limb pain, central pain, neuropathic pain such as diabetic neuropathy and postherpetic neuropathy, gastrointestinal pain disorders including, but not limited to irritable bowel syndrome, symptomatic GERD, hypersensitive esophagus, non-ulcer dyspepsia, noncardiac chest pain, biliary dyskinesia, sphincter of oddi dysfunction, and genitourinary pain disorders including but not limited to interstitial cystitis (irritable bladder), and chronic pelvic pain (including, but not limited to vulvodynia, prostatodynia and proctalgia)), Raynaud's syndrome, Parkinson's Disease, epilepsy, and others. Compounds and compositions of the present invention may also be useful for the inducement of cognitive enhancement in patients suffering from senile dementia, Alzheimer's disease, memory loss, amnesia and amnesia syndrome, and in regimens for cessation of smoking or other tobacco uses.

In some preferred embodiments of the invention, ODV formate is useful for the treatment of depression, anxiety, panic disorder, generalized anxiety disorder, post traumatic stress, premenstrual dysphoric disorder, vasomotor flushing, irritable bowel syndrome and attention deficit disorder.

This invention provides methods of treating, preventing, inhibiting or alleviating each of the maladies listed above in a mammal, preferably in a human, the methods comprising administering an effective amount of a compound of the invention to a the mammal in need thereof. An effective amount is an amount sufficient to prevent, inhibit, or alleviate one or more symptoms of the aforementioned conditions.

The dosage amount useful to treat, prevent, inhibit or alleviate each of the aforementioned conditions will vary with the severity of the condition to be treated and the route of administration. The dose, and dose frequency will also vary according to age, body weight, response and past medical history of the individual patient. In generally the recommended daily dose range for the conditions described herein lie within the range of 10 mg to about 1000 mg O-desmethylvenlafaxine per day and more preferably within the range of about 15 mg to about 350 mg/day and more preferably from about 15 mg to about 140 mg/day. In other embodiments of the invention the dosage will range from about 30 mg to about 90 mg/day. Dosage is described in terms of the free base and is adjusted accordingly for the formate salt. In managing the patient it is generally preferred that the therapy be initiated at a lower dose and increased if necessary.

For adjunctive therapy a dosage of O-desmethylvenlafaxine may be provided in combination with venlafaxine. The dosage of venlafaxine is preferably about 75 mg to about 350 mg/day and more preferably about 75 mg to about 225 mg/day. Still more preferably the dosage is about 75 mg to about 150 mg/day. The ratio of O-desmethylvenlafaxine to venlafaxine will vary from patient to patient depending upon a patient's response rate, but generally will be at least 6:1 O-desmethylvenlafaxine to venlafaxine.

Any suitable route of administration can be employed for providing the patient with an effective amount of ODV formate. For example, oral, mucosal (e.g. nasal, sublingual, buccal, rectal or vaginal), parental (e.g. intravenous or intramuscular), transdermal, and subcutaneous routes can be employed. Preferred routes of administration include oral, transdermal and mucosal.

O-desmethyl venlafaxine formate salt can be combined with a pharmaceutically acceptable carrier or excipient according to conventional pharmaceutical compounding techniques to form a pharmaceutical composition or dosage form. Suitable pharmaceutical carriers or excipients include, but are not limited to, those described in Remington's, *The Science and Practice of Pharmacy*, (Gennaro, A. R., 19$^{th}$ edition, 1995, Mack Pub. Co.) which is herein incorporated by reference. The phrase pharmaceutically acceptable refers to additives or compositions that are physiologically tolerable and do not typically produce an allergic or similar untoward reaction such as gastric upset, dizziness and the like, when administered to an animal, such as a mammal (e.g. human). For oral liquid pharmaceutical compositions, pharmaceutically acceptable carriers and excipients can include, but are not limited to water, glycols, oils, alcohols, flavoring agents, preservatives, coloring agents, and the like. Oral solid pharmaceutically acceptable excipients may include, but are not limited to starches, sugars, microcrystalline cellulose, diluents, granulating agents, lubricants, binders and disintegrating agents. The pharmaceutical composition or dosage form may also include venlafaxine or a salt thereof as discussed above.

Dosage forms include, but are not limited to tablets, capsules, troches, lozenges, dispersions, suspensions, suppositories, ointments, cataplasms, pastes, powders, creams, solutions, capsules (including encapsulated spheroids), and patches. Most preferably tablets and capsules are the dosage form. Tablets and spheroids may be coated by standard aqueous and nonaqueous techniques as required.

Each dosage form generally contains from about 15 to about 350 mg of ODV formate (as measured by the free base equivalent). More preferably each dosage form contains from about 30 to about 200 mg of ODV formate (as measured by the free base equivalent). Even more preferably each dosage form contains from about 75 to about 150 mg of ODV formate (as measured by the free base equivalent).

According to one preferred embodiment, the pharmaceutical composition is an extended release formulation, such as that described in U.S. Pat. No. 6,274,171, which is herein incorporated by reference.

According to another preferred embodiment the pharmaceutical composition is a sustained or controlled release formulation which may comprise ODV formate, a rate controlling polymer (i.e. a material which controls the rate at which ODV formate is released from the dosage form), and optionally other adjuvants. Examples of rate controlling polymers include, but are not limited to hydroxy alkyl cellulose, hydroxypropyl alkylcellulose where alkyl is 1 to 7 carbons selected from methyl, ethyl, isopropyl, butyl, penty, and hexyl and wherein the cellulose component is from 9,000 to 1,250,000 molecular weight, such as hydroxypropyl methyl cellulose, hydroxypropylethylcellulose, hydroxypropylisopropylcellulose, hydroxypropylbutylcellulose and hydroxypropylhexylcellulose; poly(ethylene)oxide, alkyl cellulose, such as ethyl cellulose and methyl cellulose; carboxymethyl cellulose; hydrophilic cellulose derivatives, and polyethylene glycol. In some preferred embodiments, the rate controlling polymer is hydroxypropyl alkyl cellulose, and more preferable hydroxypropylmethylcellulose.

A sustained release formulation may contain from about 30% to about 50% of ODV formate and from about 25 to about 70% of a rate controlling polymer.

In other embodiments of the present invention, the pharmaceutical composition is a sustained release formulation which may comprise ODV formate, a rate controlling polymer as described above and a water swellable polymer such as an acryl derivative. Acryl derivatives include, but are not limited to polyacrylates, polyethylacrylates, ethyl acrylates, methyl methacrylates, methyl methacrylates, polymethylacrylate trimethylammonium ethyl methacrylate chlorides, polyethylacrylate trimethylammonium ethyl methacrylate chlorides, dimethylaminoethyl methacrylate methacrylate copolymers, Carbopol 971P, Carbopol 974P and Carbopol 71G. In some preferred embodiments of the present invention the swellable polymer is Carbopol, and more preferably Carbopol 71G.

Pharmaceutical compositions of the present invention may comprise from about 30 to about 50 weight percent of ODV formate and from about 25 to about 70 weight percent of a rate controlling polymer. In other embodiments of the invention, pharmaceutical compositions of the invention comprise from about from about 20 to about 50 weight percent of ODV formate, from about 25 to about 45 weight percent of a rate controlling polymer and from about 25 to about 45 of a water swellable polymer. Still more preferably, the composition may comprise from about 20 to about 30 weight percent of ODV formate, from about 25 to about 35 weight percent of a rate controlling polymer and from about 25 to about 35 weight percent of a water swellable polymer. In still other preferred aspects of the invention, the composition may comprise about 23 weight percent of ODV formate, about 30 weight percent of a rate controlling polymer and about 30 percent of a water swellable polymer.

The following examples are illustrative but are not meant to be limiting of the present invention.

EXAMPLE A

Preparation of O-desmethylvenlafaxine Free Base

Dodecanethiol (122 g), venlafaxine (111 g), and a methanolic solution of sodium methanolate (30%, 90 g) and PEG 400 are heated to 190° C. The methanol is distilled off and the solution is stirred for 2 hours at 190° C. Then the temperature is lowered, 2-propanol (450 g) is added and the pH is adjusted to 9.5 with aqueous HCl. The precipitate is collected by suction filtration, and the cake is washed with 2-propanol, toluene, 2-propanol and water. The wet O-desmethylvenlafaxine is dried in vacuo.

Yield: 87 g.

$^1$H-NMR: (Gemini 200, Varian, 200 MHz) (DMSO-$d_6$) $\delta$=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7–0.8 (m, 10H, c-hex).

EXAMPLE B

Preparation of O-desmethylvenlafaxine Free Base

Venlafaxine (5.6 g) and benzenethiol sodium salt (6.9 g) are charged to PEG 400 (25 g). The reaction mixture is heated to 160° C. for 5 hours. Then the temperature is lowered and water is added (60 g). The pH is adjusted to 3.5 with $H_3PO_4$. The organic by-products are removed by extraction with heptanes (25 g). The pH of the aqueous layer is then adjusted to 9.5 with aqueous ammonia. The precipitate is collected by suction filtration, re-slurried in water (100 g), isolated by suction filtration and dried in vacuo.

Yield 1 g.

$^1$H-NMR: (Gemini 200, Varian, 200 MHz) (DMSO-$d_6$) $\delta$=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7–0.8 (m, 10H, c-hex).

EXAMPLE C

Preparation of O-desmethylvenlafaxine Free Base

Dodecanethiol (69 g), venlafaxine (55 g), and an ethanolic solution of sodium ethanolate (21%, 82 g) are charged to a pressure vessel. The temperature is raised to 150° C. and the reaction mixture is stirred for 2 days. Then the temperature is lowered and the solution is filtered. The pH of the filtrate is adjusted to 9.5 with aqueous hydrogen chloride. The crystals are collected by suction filtration. The cake is washed with ethanol and dried in vacuo.

Yield: 42 g $^1$H-NMR: (Gemini 200, Varian, 200 MHz) (DMSO-$d_6$) $\delta$=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7–0.8 (m, 10H, c-hex).

EXAMPLE D

Preparation of O-desmethylvenlafaxine Free Base

A 12 L multi-necked flask, equipped with a mechanical stirrer, a thermometer, a 1 L pressure equalizing dropping funnel, and a Claisen distillation head equipped with a downward condenser attached to a 5 L receiver with a vacuum take-off, was placed in a heating mantle. The system was purged with nitrogen and a nitrogen atmosphere was maintained. The distillation flask was charged with 4.00 L (4.00 mol, 5.55 molar excess) of 1 M L-selectride. The dropping funnel was charged with a solution of 200.00 g (0.720 mol) of venlafaxine base in 0.6936 kg (800 mL) of anhydrous 1,2-dimethoxyethane while maintaining the nitrogen atmosphere. The solution of venlafaxine base was added to the stirred L-selectride solution over a period of 15 minutes using rinses of 1,2-dimethoxyethane (2×400 mL, 2×0.3468 kg). Hydrogen was vented and bubbled through a dispersion tube into water. No significant temperature change occurred during the addition.

The dropping funnel was replaced with a similar 4 L funnel charged with 2.4276 kg (2800 mL) of anhydrous 1,2-dimethoxyethane. The system was again purged with nitrogen and a nitrogen atmosphere was maintained. The solution was heated and distilled at atmospheric pressure until the liquid level reached the 4 L mark and the reaction flask temperature was 84–85° C. While distilling, 2.4276 kg (2800 mL) of 1,2-dimethoxyethane was added dropwise at a rate which maintained the liquid level at the 4.00 L level until the temperature in the reaction flask reached 93–94° C. A crystalline precipitate was observed. The distillate was discarded.

The stirred slurry of crystals was cooled to 90° C., the stirrer was stopped, and the dropping funnel and distillation equipment was removed. The flask was then equipped with a reflux condenser fitted with a nitrogen inlet. The system was purged with nitrogen and a nitrogen atmosphere was maintained. The slurry was stirred and heated at reflux under a nitrogen atmosphere for about 19 hours. The initial temperature of the slurry at reflux was 94–96° C. and the final temperature was 97° C. Copious crystallization occurred. The slurry was cooled to room temperature.

12 L of distilled water in a 20 L Duran flask was purged with nitrogen to remove oxygen and carbon dioxide. The purging was repeated as necessary. This water is hereinafter referred to as "nitrogen purged distilled water".

The heating mantle was removed and replaced with an ice/water bath to bring the temperature of the reaction mixture to near room temperature. The flask was equipped with a 1000 mL pressure equalizing dropping funnel. The stirred reaction mixture was cooled with an ice/alcohol bath to obtain a temperature of 15–20° C. While the nitrogen atmosphere was maintained, the reaction mixture was quenched by dropwise addition of 0.296 kg (296 mL) of the nitrogen purged distilled water. The addition was controlled so as to maintain the temperature below 25° C. The temperature rose to 15–24° C. as a result of an exotherm. The mixture was stirred at ambient temperature for about 1 hour. A thick gel-like precipitate, which was formed initially, was converted into a crystalline precipitate during this period. While the reaction mixture was maintained in the nitrogen atmosphere, the flask was equipped with a Claisen distillation head, a downward condenser with a vacuum take-off and a 5 L receiving flask chilled in an ice/water bath. The stirred reaction mixture was distilled under pump vaccum (109–134 mm Hg) down to the 2.80 L mark at a distillation flask temperature of 25–38° C. The distillate was discarded. 3.00 kg (3000 mL) of nitrogen purged distilled water was added.

The stirred mixture was distilled under pump vacuum (113–187 mm Hg) down to 2.80 L at a distillation flask temperature of 35–50° C. to form a biphasic mixture. The distillate (Distillate A) was discarded by the Waste Treatment procedure described below. The warm biphasic mixture (35–40° C.) was transferred to a 4 L separatory funnel using rinses of 600 mL of nitrogen purged distilled water and 0.5296 kg (600 mL) of toluene. The two phases were mixed and then allowed to separate. A small quantity of solid at the interface was discarded. The aqueous layer was extracted consecutively with toluene (2×0.5196 kg, 2×600 mL) and heptane (0.5472 kg, 800 mL). The organic phases (Extract A) were discarded by the Waste Treatment procedure described below. A sufficient amount of nitrogen purged distilled water was added to the aqueous layer to achieve a volume of 3.60 L.

A 12 L multi-necked flask was equipped with a mechanical stirrer, a thermometer, and a condenser with a nitrogen inlet. The flask was purged with nitrogen and a nitrogen atmosphere was maintained in the flask.

The 3.60 L aqueous layer was transferred to the empty 12 L flask. The stirred solution was cooled under nitrogen to 10–15° C. with an ice/water bath. From a 1000 mL pressure equalizing dropping funnel, 410 mL of 12 N hydrochloric acid was added dropwise to the stirred solution while maintaining the temperature at 10–15° C. with the ice/water bath and until a pH of 3.5±0.2 was reached. A small precipitate was formed.

The resulting suspension was filtered through a Celite pad on polypropylene cloth in a 19 cm Buchner funnel into a 5 L multi-necked flask equipped with a mechanical stirrer, a thermometer, a condenser with a nitrogen inlet and a 1000 mL pressure equalizing dropping funnel. The filter pad was washed with 300 mL of nitrogen purged distilled water.

The filter funnel was removed. The system was flushed with nitrogen and again maintained in a nitrogen atmosphere. To the stirred solution, 76 mL of 10 N sodium hydroxide was added from the dropping funnel until a pH of 9.6±0.2 was reached. The resulting slurry of crystals was cooled to 5–10° C. and the slurry of crystals was maintained at 0–5° C. for about 1 hour.

The solid was collected on a polypropylene cloth in a 19 cm Buchner funnel. The filter cake was washed with 3×200 mL of nitrogen purged distilled water. The filtrate was discarded.

A 12 L multi-necked flask was equipped with a mechanical stirrer, a thermometer, and a condenser with a nitrogen inlet. The flask was purged with nitrogen and a nitrogen atmosphere was maintained in the flask. The flask was charged with 3000 mL of nitrogen purged distilled water and cooled to 15–20° C. with an ice/water bath. The solids collected on the polypropylene cloth were added to the stirred water in the flask and stirred at 15–20° C. until a smooth suspension was obtained (about 30 minutes).

The solid was collected on a polypropylene cloth in a 19 cm Buchner funnel using 600 mL of nitrogen purged distilled water to complete the transfer. The filter cake was washed with water (3×300 mL) and filtered. A dam was formed on top of the filter with a sheet of latex rubber and an aspirator vacuum was applied to the filter flask for about 5 hours. The white solid was dried in a vacuum oven under oil pump vacuum at 80° C. for about 18 hours. The solid was crushed and re-dried if necessary to constant weight. The yield was 90.7% (172.3 g) (HPLC Analysis:Strength or Purity (w/w): 98.8%, Impurities (excluding inorganics) (w/w): 0.046%, Ash (inorganics) (w/w): 0.14%).

Waste Treatment

The waste to be discarded contained byproducts, such as tris(1-methylpropyl)-borane and tris(1-methylpropyl)-boroxin. A 22 L or 50 L multi-necked flask was equipped with a mechanical stirrer, a thermometer, and a condenser with a nitrogen inlet. The flask was purged with nitrogen using a Firestone valve and a nitrogen atmosphere was maintained in the flask.

Distillate A and Extract A were combined in the flask to obtain a biphasic mixture (4.00 L with 400 mL of an aqueous bottom phase) under a nitrogen atmosphere. The stirrer was started and 600 mL of 10 N sodium hydroxide and 600 mL of water were added. A slurry of sodium perborate tetrahydrate (1.848 kg, 12.01 moles, ~3 equivalents per mole of tris(1-methylpropyl)borane) in 12 L of water was added in portions with ice/water cooling over about 20 minutes to maintain the temperature at 28–38° C. After the exotherm had subsided, the mixture was stirred at 22–23° C. under a nitrogen atmosphere for about 18 hours. The solid dissolved and two liquid phases remained.

The stirrer was stopped and the phases were allowed to separate. The upper phase was examined by gas chromatography/mass spectrometry to determine if any tris(1-methylpropyl)borane or tris(1-methylpropyl)boroxin was still detectable. If any was detected, 80 g (0.52 mol) of sodium perborate was added as a slurry in 400 mL of water and the solution was stirred at 22–23° C. for about 18 hours. Once tris(1-methylpropyl)borane and tris(1-methylpropyl)boroxin were no longer detectable in the upper phase, the aqueous phase was checked for its oxidizing capability (for example, due to peroxides and excess sodium perborate) with starch iodide paper.

The phases of the solution were then separated. The top organic layer was combined with other organic waste from the synthesis to be discarded. The aqueous layer was combined with other aqueous waste from the synthesis to be discarded.

EXAMPLE 1

Preparation of O-desmethylvenlafaxine Formate

A mixture of O-desmethylvenlafaxine (23.9 g), 96 wt % formic acid (4.79 g) and 2B ethanol (100 mL) was evaporated to give a syrupy residue. This material was redissolved in 2 B ethanol (100 mL) and evaporated to give a solid, which upon trituration in ether (200 mL) followed by filtration and vacuum drying (18 h; 50° C.; 50 mmHg) gave 27 g of product. This material was recrystallized from a hot solution of methanol (30 mL) and acetone (400 mL), which upon cooling to room temperature followed by filtering and vacuum drying (18 h; 50° C.; 50 mmHg) gave 20 g (71.2% yield) of product. m.p. 151° C.

Analysis for $C_{16}H_{25}NO_2 \cdot CH_2O_2$: Calculated: C, 65.99; H, 8.80; N, 4.53; Found: C, 65.34; H, 8.69; N, 4.46.

$^1$H NMR (Bruker DRX, 400 MHz): $^1$H ($d_6$-DMSO) multiplet 0.92 δ (1H); multiplet 1.10 δ (2H); multiplet 1.34 δ (3H); multiplet 1.42–1.61 δ (4H); singlet 2.38 δ (6H); double doublet 2.83 δ (1H) double doublet 2.89 δ (1H) double doublet 3.31 δ (1H); doublet 6.69 δ (2H); doublet 7.04 δ (2H); singlet 8.34 δ (1H); broad singlet 8.40–8.80 δ(3H).

EXAMPLE 2

Preparation of O-desmethylvenlafaxine Formate

To a stirred solution of O-desmethylvenlafaxine (13.17 g, 0.050 mol.) in tetrahydrofuran (300 mL) at 62–65° C., under a nitrogen atmosphere, was added 96 wt % formic acid (2.20 mL, d=1.22, 0.056 mol., 1.2 molar excess) in tetrahydrofuran (30 mL) dropwise over a period of 2 minutes, while maintaining the temperature in the range 62° C.–64° C. The solution was filtered through a pad of Celite filter aid (prewashed with tetrahydrofuran) and the filter pad was washed with hot (60–65° C.) tetrahydrofuran (2×20 mL). The filtrate and washings (temperature ~35° C.) were warmed to 50° C. under a nitrogen atmosphere and allowed to cool. At 48° C. the stirred solution was seeded with crystals of O-desmethylvenlafaxine formate. Crystallization ensued immediately. When the slurry of crystals had cooled to 22° C. it was chilled to –5° C. to –10° C. The crystals were collected on a filter and washed with chilled (–5 to –10° C.) tetrahydrofuran (2×30 mL). After drying in a vacuum oven at room temperature under oil pump vacuum for 23 hours the product, O-desmethylvenlafaxine formate, weighed 13.79 g, (89% yield) and it had mp=149 150° C. It was characterized by DSC (sharp endotherm at 151.5° C.).

EXAMPLE 3

Preparation of O-desmethylvenlafaxine Formate

To a stirred suspension of O-desmethylvenlafaxine (39.51 g, 0.150 mol) in acetone (1500 mL) at 55–60° C., under a nitrogen atmosphere, was added a solution of 96% formic acid (13.5 mL, d=1.22, 2.29 molar excess) in acetone (150 mL) over a period of 10 min. The stirred mixture was kept at 55–60° C. for a further 5 min. to complete the dissolution. The warm solution was filtered through a pad of Celite filter aid (prewashed with warm acetone) and the filter pad was washed with warm acetone (150 mL). The filtrate and washings (temperature ~35° C.) were warmed to 45° C. under a nitrogen atmosphere and seeded with crystals of O-desmethyl-venlafaxine formate. The stirred solution was allowed to cool. Crystallization ensued and was copious after 1 hour (when the temperature had fallen to 30° C.). The slurry of crystals at 27° C. was chilled to –10° C. over a period of half an hour and maintained at –5–-10° C. for 15 min. The crystals were then collected on a filter and washed with chilled (–5 to –10° C.) acetone (2×100 mL). After drying in a vacuum oven at room temperature under oil pump vacuum for 24 hours, the product, O-desmethylvenlafaxine formate, weighed 38.5 g, (83% yield) and it had mp=148° C.-149.5° C. It was characterized by DSC (sharp endotherm at 152.4° C.).

EXAMPLE 4

Preparation of O-desmethylvenlafaxine formate

To a mechanically stirred suspension of O-desmethylvenlafaxine (100.0 g, 0.380 mol) in 2-propanol (500 mL) at 70–75° C. under a nitrogen atmosphere was added dropwise a solution of 96% formic acid (20 ml, d=1.22, 23.42 g, 0.509 mol., 1.34 molar excess) over a period of 45 min. The resulting, hazy solution was kept for a further 10 min. at 70–75° C. and then filtered through a pad of Celite filter aid (20 g, prewashed with hot 2-propanol). The filter pad was washed with hot (70–75° C.) 2-propanol (2×81 mL). The filtrate and washings (temperature 44–45° C.) were warmed to 50° C., under a nitrogen atmosphere, using slow mechanical stirring. The solution was seeded with crystals of O-desmethylvenlafaxine formate and allowed to cool. After further seeding at 45° C. the solution was allowed to cool to 40–41° C. whereupon the solution became cloudy. The stirred, cloudy solution was maintained at 40–42° C. for 25 min. and then cooled quickly (using cold water) to 35° C. It was then maintained at 34–35° C. for 1.5 h. Copious crystallization occurred during this latter period. The stirred thick slurry of crystals was allowed to cool to 25° C. over a period of 50 min. and then cooled to 7° C. (using ice) over a period of 1 h. and 40 min. The slurry was chilled to −10° C. in 10 min. and kept at that temperature for 30 min. The crystals were collected on a filter and washed with chilled (−5 to −10° C.) acetone (3×200 mL). After drying in a vacuum oven at 46–47° C., for 47 h. at 80 mm Hg, under a nitrogen stream, the product, O-desmethylvenlafaxine formate, weighed 101.59 g (86% yield) and it had mp=146.5–148° C. It was characterized by DSC (sharp endotherm at 152.4° C.).

EXAMPLE 5

Preparation of O-desmethylvenlafaxine Formate

To a mechanically stirred suspension of O-desmethylvenlafaxine (200.0 g, 0.759 mol in 2-propanol (1000 mL) at 70–75° C. under a nitrogen atmosphere was added dropwise a solution of 96% formic acid (40 ml, d=1.22, 46.85 g, 1.018 mol., 1.34 molar excess) over a period of 1 hour. The resulting, hazy solution was kept for a further 10 min. at 70–75° C. and then filtered through a pad of Celite filter aid (40 g, prewashed with hot 2-propanol). The filter pad was washed with hot (70–80° C.) 2-propanol (2×162 mL). The filtrate and washings (temperature 48–49° C.) were stirred slowly under a nitrogen atmosphere and allowed to cool to 45° C. The solution was seeded with crystals of O-desmethylvenlafaxine formate and allowed to cool at a rate of about 1° C. per 4 minutes. The solution became cloudy at 40.5° C. The stirred, cloudy solution was allowed to cool to 34–35° C., then maintained at that temperature for a period of 1.5 hours. Most of the product crystallized during this period. The stirred slurry of crystals was allowed to cool to 25° C. over a period of 1 hour and then cooled in an ice bath over a period of 1 hour to 5–10° C. The slurry was chilled to −10° C. in 40 min. and kept at that temperature for 30 min. The crystals were collected on a filter and washed with chilled (0 to −10° C.) acetone (3×400 mL). Drying in a vacuum oven at 47–48° C., for 36 hours at 80 mm Hg, under a nitrogen stream, (with intermediate crushing after 13 hours) furnished 203.1 g (86%) of the product, O-desmethylvenlafaxine formate. The product had a mp=145–147° C. and residue on ignition 0.1% (as sulfated ash). It was characterized by DSC (sharp endotherm at 151.8° C.

The following procedures were used to analyze the product of Examples 1–5.

Differential Scanning Calorimetry (DSC)

Figure 1:
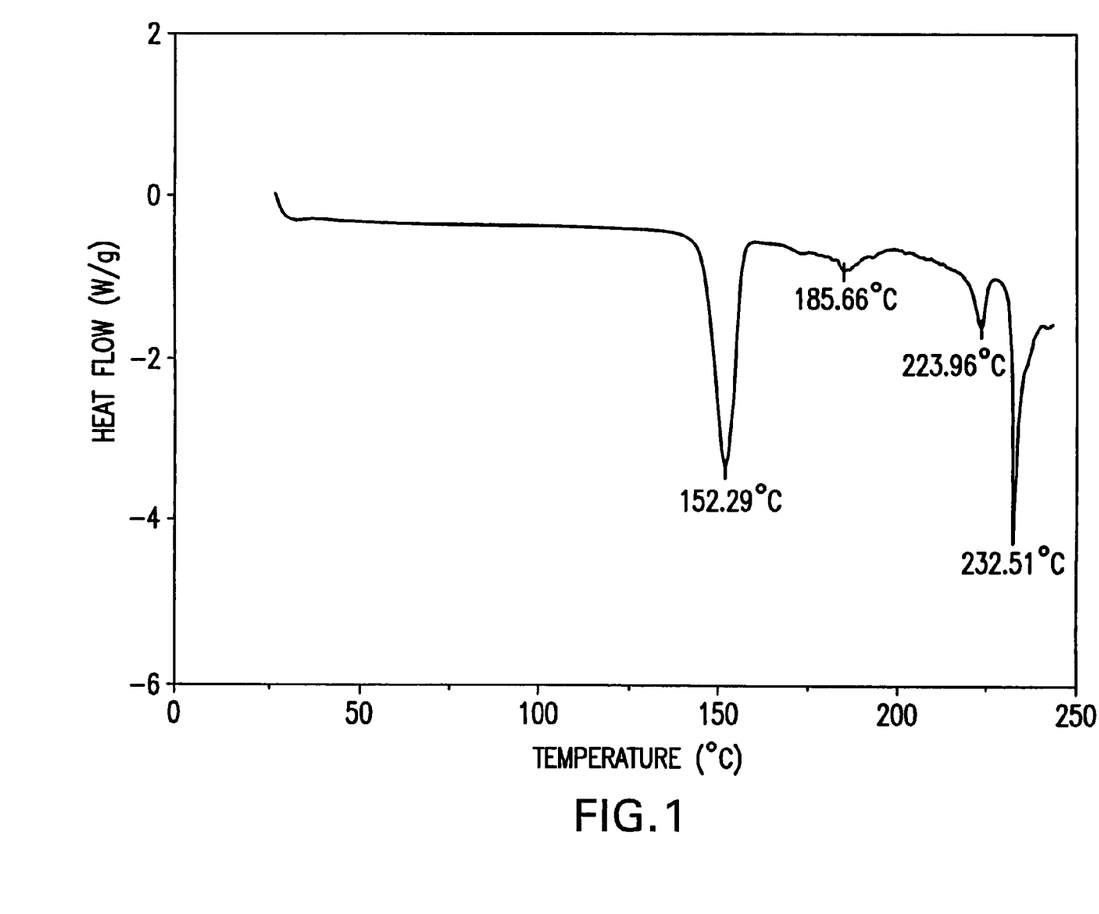
FIG. 1 is a differential scanning calorimetry (DSC) analysis of ODV formate.

DSC analysis was carried out on a TA Instrument differential scanning calorimeter 2920. Approximately 10 mg of sample was placed in a DSC pan, and the weight accurately recorded. The pan was hermetically sealed. Each sample was heated under nitrogen at a rate of 10° C./minute from 30° C. up to a final temperature of 250° C. Indium and lead metal were used as calibration standards. The results of DSC for Example 1 is shown in FIG. 1. The scan exhibits two relatively sharp endotherms at 152° C. and 232° C., a small endotherm at 224° C. and a small broad endotherm at 186° C. O-desmethylvenlafaxine formate has a sharp endotherm at about 152° C.

Thermogravimetric Analysis (TGA)

Figure 2:
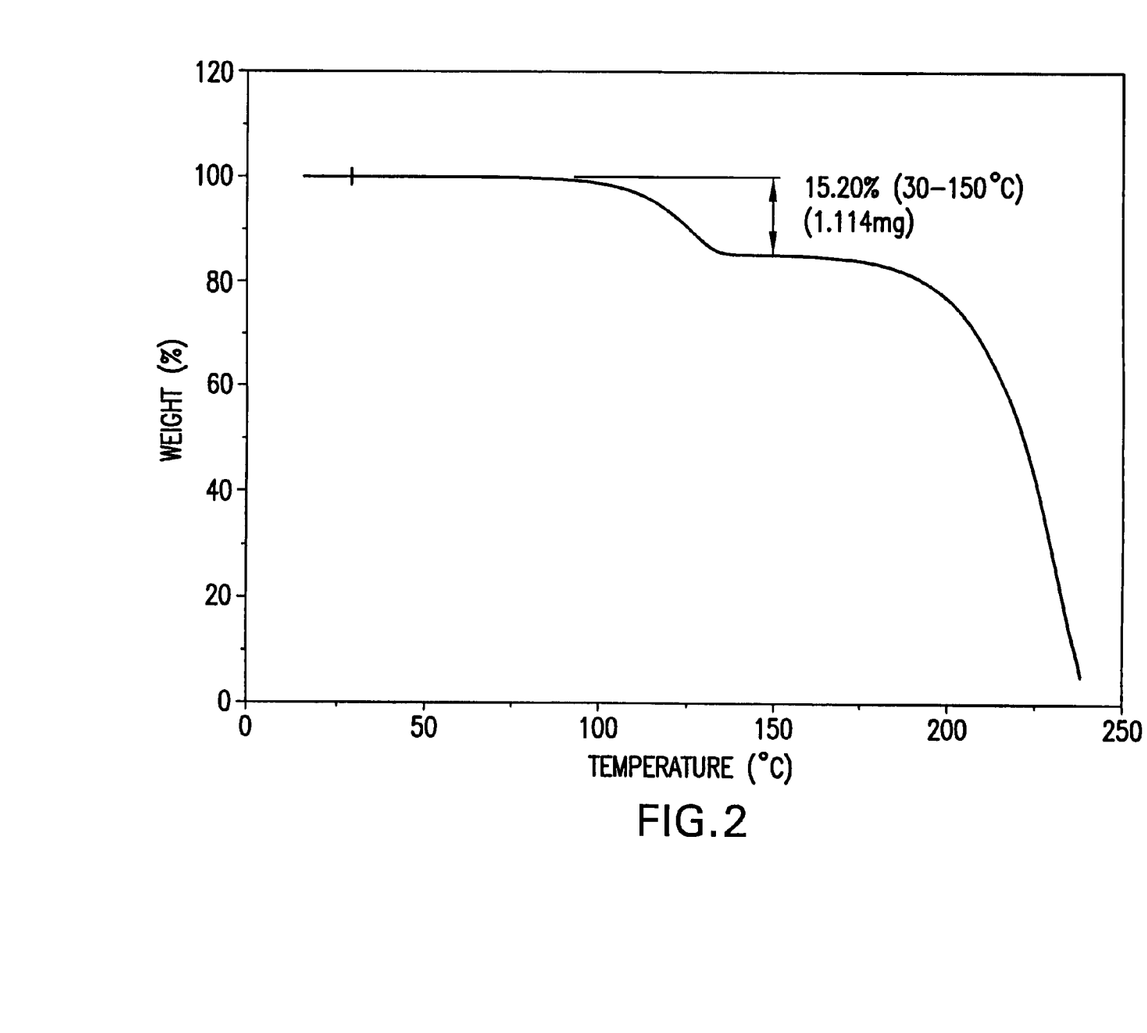
FIG. 2 is a thermogravimetric analysis of ODV formate.

TGA was conducted on a TA Instruments 2950 thermogravimetric analyzer. The daily check was performed with calcium oxalate standard. Approximately 8–20 mg were placed in the pan accurately weighed, and inserted into the TG furnace. The samples were heated under helium at a rate of 10° C./min, up to a final temperature of 250° C. Weight loss was calculated from 30–150° C. The material was heated from room temperature to 250° C. and monitored for changes in mass. A well defined loss of 15.2% was seen from 75° C. to 130° C., most likely corresponding to loss of formic acid (14.9% by weight theoretical). A nearly complete loss of remaining mass was seen beginning at 175° C. and ending at approximately 250° C., corresponding to decomposition or sublimation/boiling. The results are shown in FIG. 2.

X-Ray Powder Diffraction

Figure 3:
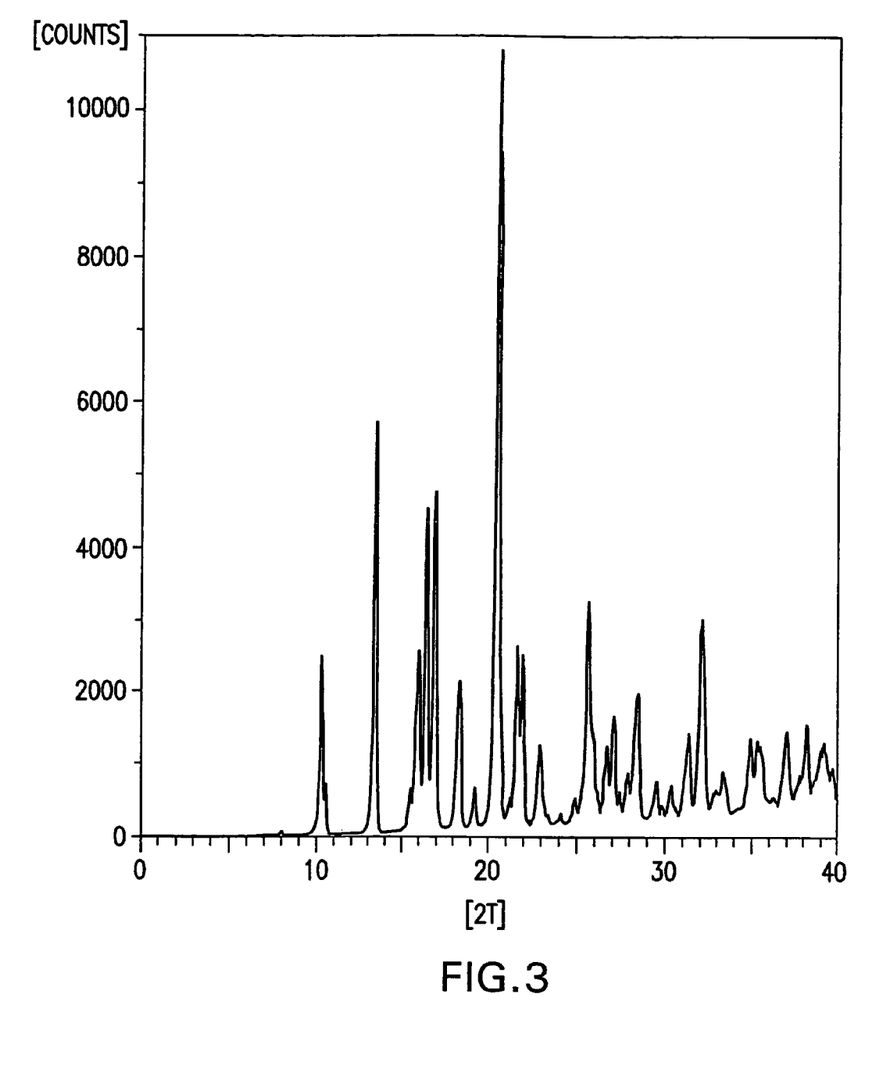
FIG. 3 is an XRPD of ODV formate.

XRPD analyses were carried out on a Philips PW3040-MPD diffractometer using Cu K αradiation. The instrument is equipped with a long line focus X-ray tube. The tube voltage and anode current were set at 40 kV and 40 mA, respectively. The divergence and scattering slits were set on automatic and the receiving slit was set at 0.30 mm. Diffracted radiation was detected by a proportional Xe filled detector. A θ–2θcontinuous scan at 1.2 deg/min (1 s/0.02 deg step) from 4.0 to 40 deg 2θ was used. A silicon powder standard was analyzed each day to check the instrument alignment. The X-ray diffractogram shown in FIG. 3 evidences the crystal nature of the product.

EXAMPLE 6

| Hard Gelatin Capsule Dosage Form | | |
| --- | --- | --- |
| Ingredient | mg/capsule | % w/w |
| ODV formate | 88.11 (75 as free base) | 33 |
| Lactose Fast Flow | 177.3 | 66.4 |
| Magnesium Stearate | 1.5 | 0.6 |
| Total | 266.9 | 100.0 |

The active ingredient is sieved and blended with the listed excipients. Suitably sized hard gelatin capsules are filled using suitable machinery and methods well known in the art. Other doses may be prepared by altering the fill weight and, if necessary, by changing the capsule size to suit.

EXAMPLE 7

| Tablet Dosage Form A | | |
| --- | --- | --- |
| Ingredient | Mg/capsule | % w/w |
| ODV formate | 88.11 (75.00 as free base) | 29.37 |
| HPMC | 170.43 | 56.81 |
| Microcrystalline Cellulose | 33.21 | 11.07 |
| Talc USP | 6.75 | 2.25 |
| Magnesium Stearate | 1.50 | 0.50 |
| Total | 300.00 | 100.00 |

The ingredients are sieved and blended together. The tablets are compressed using suitable machinery and methods well known in the art. Other doses may be prepared by altering the strength and weight of the tablet.

EXAMPLE 8

Tablet Dosage Form B

| Ingredient | mg/capsule | % w/w |
|---|---|---|
| ODV formate | 88.11 (75 as free base) | 23.50 |
| HPMC | 112.50 | 30.00 |
| Carbopol 71G | 112.50 | 30.00 |
| Microcrystalline Cellulose | 50.64 | 13.50 |
| Talc USP | 7.50 | 2.00 |
| Magnesium Stearate | 3.75 | 1.00 |
| Total | 375.00 | 100.00 |

The ingredients are sieved and blended together. The tablets are compressed using suitable machinery and methods well known in the art. Other doses may be prepared by altering the strength and weight of the tablet.

The present invention is not to be limited in scope by specific embodiments described herein. Indeed, various modifications of the invention in addition to those described herein will become apparent to those skilled in the art from the foregoing description and accompanying figures. Such modifications are intended to fall within the scope of the appended claims.

Patents, patent applications, publications, procedures and the like are cited throughout this application, the disclosures of which are incorporated herein by reference in their entireties. To the extent a conflict may exist between the specification and a reference, the language of the disclosure made herein controls.

What is claimed:

1. O-desmethylvenlafaxine formate which is a soild.
2. O-desmethylvenlafaxine formate having an endotherm at about 152° C.
3. O-desmethylvenlafaxine formate having endotherms at about 152° C. and about 232° C.
4. O-desmethylvenlafaxine formate having a particle size from about 1.5 to about 26 μm.
5. O-desmethylvenlafaxine formate having an aspect ratio of about 1 to about 44.
6. O-desmethylvenlafaxine formate having an aspect ratio of from about 1 to about 4.
7. O-desmethylvenlafaxine formate claim 1 having a solubility in water at room temperature of at least about 425 mg/ml.

* * * * *